(12) United States Patent
Bold et al.

(10) Patent No.: US 7,067,543 B2
(45) Date of Patent: Jun. 27, 2006

(54) ANTHRANILIC ACID AMIDES AND PHARMACEUTICAL USE THEREOF

(75) Inventors: Guido Bold, Gipf-Oberfrick (CH); Pascal Furet, Thann (FR); Paul W Manley, Arlesheim (CH)

(73) Assignee: Novartis AG, Basel (CH)

( * ) Notice: Subject to any disclaimer, the term of this patent is extended or adjusted under 35 U.S.C. 154(b) by 11 days.

(21) Appl. No.: 10/494,222

(22) PCT Filed: Nov. 7, 2002

(86) PCT No.: PCT/EP02/12445

§ 371 (c)(1),
(2), (4) Date: May 3, 2004

(87) PCT Pub. No.: WO03/040101

PCT Pub. Date: May 15, 2003

(65) Prior Publication Data

US 2004/0248947 A1    Dec. 9, 2004

(30) Foreign Application Priority Data

Nov. 8, 2001    (GB) .................................. 0126901.8

(51) Int. Cl.
*C07D 213/38*    (2006.01)
*A61K 31/44*    (2006.01)

(52) U.S. Cl. ...................... 514/357; 546/336; 514/619; 564/169

(58) Field of Classification Search ................ 514/357, 514/619; 546/336; 564/169
See application file for complete search history.

(56) References Cited

U.S. PATENT DOCUMENTS 3,226,394 A * 12/1965 Schipper ..................... 546/337

FOREIGN PATENT DOCUMENTS

WO       WO 00/27820       5/2000

* cited by examiner

*Primary Examiner*—Zinna Northington Davis
(74) *Attorney, Agent, or Firm*—Lydia T. McNally

(57) ABSTRACT

The invention relates to anthranilic acid amide derivatives of formula (I), wherein Ar is represented by the subformula ($I_a$), wherein $R_a$ represents H or lower alkyl, and $R_1$ represents H or perfluoro lower alkyl, $R_2$ represents H, halogen, $C_2$–$C_7$alkyl, $C_2$–$C_7$alkenyl or lower aklynyl; or Ar is represented by the subformula ($I_b$) and $R_1$ represents perfluoro lower alkyl, and $R_2$ represents bromo, iodo, $C_2$–$C_7$alkyl, $C_2$–$C_7$alkenyl or lower alkynyl, or $R_1$ represents H, and $R_2$ represents fluoro, bromo, iodo, ethyl, $C_5$–$C_7$alkyl, $C_2$–$C_7$alkenyl or lower alkynyl; to N-oxides and tautomers thereof, and to salts of such anthranilic acid amides, its N-oxides and tautomers; to processes for their preparation; to their application in the treatment of the human or animal body, to the use thereof—alone or in combination with one or more other pharmaceutically active compounds—for the treatment especially of a neoplastic disease, such as a tumor disease, of retinopathy or age-related macular degeneration; to a method for the treatment of such diseases in animals; and to the use of such a compound—alone or in combination with one or more other pharmaceutically active compounds—for the manufacture of a pharmaceutical preparation for the treatment of a neoplastic disease, of retinopathy or age-related macular degeneration.

10 Claims, No Drawings

ANTHRANILIC ACID AMIDES AND PHARMACEUTICAL USE THEREOF

The invention relates to new anthranilic acid amide derivatives, processes for the preparation thereof, the application thereof in a process for the treatment of the human or animal body, the use thereof—alone or in combination with one or more other pharmaceutically active compounds—for the treatment especially of a neoplastic disease, such as a tumor disease, of retinopathy and age-related macular degeneration; a method for the treatment of such a disease in animals, especially in humans, and the use of such a compound—alone or in combination with one or more other pharmaceutically active compounds—for the manufacture of a pharmaceutical preparation (medicament) for the treatment of a neoplastic disease, of retinopathy or age-related macular degeneration.

Certain diseases are known to be associated with deregulated angiogenesis, for example diseases caused by ocular neovascularisation, such as retinopathies (including diabetic retinopathy), age-related macular degeneration, psoriasis, haemangioblastoma, haemangioma, arteriosclerosis, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumours and liquid tumours (such as leucemias).

At the centre of the network regulating the growth and differentiation of the vascular system and its components during embryonic development, normal growth and in a wide number of pathological anomalies and diseases, lies the angiogenic factor known as "Vascular Endothelial Growth Factor" (VGEF), a dimeric, disulfide-linked 46-kDa glycoprotein, along with its cellular receptors (see Breier, G., et al., Trends in Cell Biology 6, 454–6 [1996]).

VEGF receptors are transmembranous receptor tyrosine kinases. Various types of VEGF receptor are known, e.g. VEGFR-1, VEGFR-2, and VEGFR-3.

A large number of human tumors, especially gliomas and carcinomas, express high levels of VEGF and its receptors. This has led to the hypothesis that the VEGF released by tumor cells could stimulate the growth of blood capillaries and the proliferation of tumor endothelium in a paracrine manner and thus, through the improved blood supply, accelerate tumor growth. Direct evidence of the role of VEGF as a tumor angiogenesis factor in vivo has been obtained from studies in which VEGF activity was inhibited by antibodies.

Angiogenesis is regarded as an absolute prerequisite for those tumors which grow beyond a maximum diameter of about 1–2 mm; up to this limit, oxygen and nutrients may be supplied to the tumor cells by diffusion.

Three principal mechanisms play an important part in the activity of angiogenesis inhibitors against tumors: 1) inhibition of the growth of vessels, especially capillaries, into a vascular resting tumors, with the result that there is no net tumor growth owing to the balance that is achieved between apoptosis and proliferation; 2) prevention of the migration of tumor cells owing to the absence of blood flow to and from tumors; and 3) inhibition of endothelial cell proliferation, thus avoiding the paracrine growth-stimulating effect exerted on the surrounding tissue by the endothelial cells which normally line the vessels.

In WO00/27820 compounds are described belonging to the class of anthranilic acid amides which compounds are reported to inhibit the activity of the VEGF receptor tyrosine kinase, the growth of tumors and VEGF-dependent cell proliferation.

Surprisingly, it has now been found that the anthranilic acid amide derivatives of formula I, described below, have advantageous pharmacological properties and inhibit, for example, the activity of the VEGF receptor tyrosine kinase, the growth of tumors and VEGF-dependent cell proliferation.

The anthranilic acid amide derivatives of formula I are suitable, for example, to be used in the treatment of diseases, especially for diseases in the treatment and also for the prevention of which, an inhibition of angiogenesis and/or of the VEGF receptor tyrosine kinase shows beneficial effects.

The invention pertains to anthranilic acid amides of formula I,

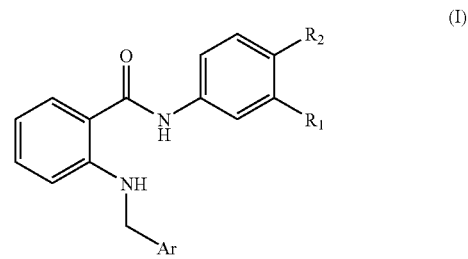

wherein Ar is represented by the subformula $I_a$

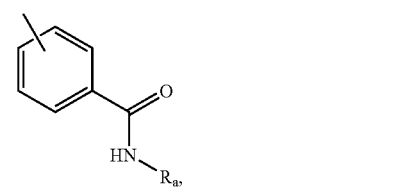

wherein $R_a$ represents H or lower alkyl, $R_1$ represents H or perfluoro lower alkyl, and $R_2$ represents H, halogen, $C_2$–$C_7$alkyl, $C_2$–$C_7$alkenyl or lower alkynyl; or Ar is represented by the subformula $I_b$,

and $R_1$ represents perfluoro lower alkyl, and $R_2$ represents bromo, iodo, $C_2$–$C_7$alkyl, $C_2$–$C_7$alkenyl or lower alkynyl, or $R_1$ represents H, and $R_2$ represents fluoro, bromo, iodo, ethyl, $C_5$–$C_7$alkyl, $C_2$–$C_7$alkenyl or lower alkynyl, to N-oxides and tautomers thereof, and to salts of such anthranilic acid amides, their N-oxides and their tautomers.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I, wherein $R_9$ is lower alkyl) may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

In the preferred embodiment, alkyl has up to a maximum of 12 carbon atoms and is especially lower alkyl.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

The term "perfluoro lower alkyl" as used herein means a lower alkyl radical wherein all hydrogen atoms are replaced by fluoro atoms.

Halogen is especially fluorine, chlorine, bromine, or iodine, especially fluorine, chlorine, or bromine.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I and N-oxides thereof have valuable pharmacological properties, as described hereinbefore and hereinafter.

The efficacy of the compounds of the invention as inhibitors of VEGF-receptor tyrosine kinase activity can be demonstrated as follows:

Test for activity against VEGF-receptor tyrosine kinase. The test is conducted using Flt-1 VEGF-receptor tyrosine kinase. The detailed procedure is as follows: 30 μl kinase solution (10 ng of the kinase domain of Flt-1, Shibuya et al., Oncogene 5, 519–24 [1990]) in 20 mM Tris.HCl pH 7.5, 3 mM manganese dichloride ($MnCl_2$), 3 mM magnesium chloride ($MgCl_2$), 10 μM sodium vanadate, 0.25 mg/ml polyethylenglycol (PEG) 20000, 1 mM dithiothreitol and 3 μg/μl poly(Glu, Tyr) 4:1 (Sigma, Buchs, Switzerland), 8 μM [$^{33}$P]-ATP (0.2 μCi), 1% dimethyl sulfoxide, and 0 to 100 μM of the compound to be tested are incubated together for 10 minutes at room temperature. The reaction is then terminated by the addition of 10 μl 0.25 M ethylenediaminetetraacetate (EDTA) pH 7. Using a multichannel dispenser (LAB SYSTEMS, USA), an aliquot of 20 μl is applied to a PVDF (=polyvinyl difluoride) Immobilon P membrane (Millipore, USA), through a Millipore microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 μl Microscint® (β-scintillation counter liquid). $IC_{50}$-values are determined by linear regression analysis of the percentages for the inhibition of each compound in three concentrations (as a rule 0.01, 0.1, and 1 μmol). The $IC_{50}$-values that can be found with compounds of formula I are in the range of 0.001 to 1 μM, preferably in the range from 0.001 to 0.1 μM.

The antitumor efficacy of the compounds of the invention can be demonstrated in vivo as follows:

In vivo activity in the nude mouse xenotransplant model: female BALB/c nude mice (8–12 weeks old), Novartis Animal Farm, Sisseln, Switzerland) are kept under sterile conditions with water and feed ad libitum. Tumors are induced either by subcutaneous injection of tumor cells into mice (for example, Du 145 prostate carcinoma cell line (ATCC No. HTB 81; see Cancer Research 37, 4049–58 (1978)) or by implanting tumor fragments (about 25 mg) subcutaneously into the left flank of mice using a 13-gauge trocar needle under Forene® anaesthesia (Abbott, Switzerland). Treatment with the test compound is started as soon as the tumor has reached a mean volume of 100 mm$^3$. Tumor growth is measured two to three times a week and 24 hours after the last treatment by determining the length of two perpendicular axes. The tumor volumes are calculated in accordance with published methods (see Evans et al., Brit. J. Cancer 45, 466–8 [1982]). The antitumor efficacy is determined as the mean increase in tumor volume of the treated animals divided by the mean increase in tumor volume of the untreated animals (controls) and, after multiplication by 100, is expressed as T/C %. Tumor regression (given in %) is reported as the smallest mean tumor volume in relation to the mean tumor volume at the start of treatment. The test compound is administered daily by gavage.

As an alternative other cell lines may also be used in the same manner, for example:

the MCF-7 breast adenocarcinoma cell line (ATCC No. HTB 22; see also J. Natl. Cancer Inst. (Bethesda) 51, 1409–16 [1973]);

the MDA-MB 468 breast adenocarcinoma cell line (ATCC No. HTB 132; see also In Vitro 14, 911–15 [1978]);

the MDA-MB 231 breast adenocarcinoma cell line (ATCC No. HTB 26; see also J. Natl. Cancer Inst. (Bethesda) 53, 661–74 [1974]);

the Colo 205 colon carcinoma cell line (ATCC No. CCL 222; see also Cancer Res. 38, 1345–55 [1978]);

the HCT 116 colon carcinoma cell line (ATCC No. CCL 247; see also Cancer Res. 41, 1751–6 [1981]);

the DU145 prostate carcinoma cell line DU 145 (ATCC No. HTB 81; see also Cancer Res. 37, 4049–58 [1978]); and the PC-3 prostate carcinoma cell line PC-3 (ATCC No. CRL 1435; see also Cancer Res. 40, 524–34 [1980]).

The inhibition of VEGF-induced KDR-receptor autophosphorylation can be confirmed with a further in vitro experiment in cells: transfected CHO cells, which permanently express human VEGF receptor (KDR), are seeded in complete culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours' incubation at 37° C., recombinant VEGF is added; the final VEGF concentration is 20 ng/ml). After a further five minutes' incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an anti-phosphotyrosine antibody coupled with alkaline phosphatase (PY20:AP from Transduction Laboratories). The (plates are washed again and the) binding of the anti-phosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition).

A compound of formula I or a N-oxide thereof inhibits to varying degrees also other tyrosine kinases involved in signal transduction which are mediated by trophic factors, for example kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

On the basis of these studies, a compound of formula I according to the invention shows therapeutic efficacy especially against disorders dependent on protein kinase, especially proliferative diseases.

The usefulness of a compound of the formula I in the treatment of arthritis as an example of an inflammatory rheumatic or rheumatoid disease can be demonstrated as follows:

The well-known rat adjuvant arthritis model (Pearson, Proc. Soc. Exp. Biol. 91, 95–101 (1956)) is used to test the anti-arthritic activity of compounds of the formula I, or salts thereof. Adjuvant Arthritis can be treated using two different dosing schedules: either (i) starting time of immunisation with adjuvant (prophylactic dosing); or from day 15 when the arthritic response is already established (therapeutic dosing). Preferably a therapeutic dosing schedule is used. For comparison, a cyclooxygenase-2 inhibitor, such as 5-bromo-2-(4-fluorophenyl)-3-[4-(methylsulfonyl)phenyl]thiophene or diclofenac, is administered in a separate group.

In detail, male Wistar rats (5 animals per group, weighing epproximately 200 g, supplied by Iffa Credo, France) are injected i.d. (intra-dermally) at the base of the tail with 0.1 ml of mineral oil containing 0.6 mg of lyophilised heat-killed *Mycobacterium tuberculosis*. The rats are treated with the test compound (3, 10 or 30 mg/kg p.o. once per day), or vehicle (water) from day 15 to day 22 (therapeutic dosing schedule). At the end of the experiment, the swelling of the tarsal joints is measured by means of a mico-calliper. Percentage inhibition of paw swelling is calculated by reference to vehicle treated arthritic animals (0% inhibition) and vehicle treated normal animals (100% inhibition).

On the basis of these studies, a compound of formula I surprisingly is appropriate for the treatment of inflammatory (especially rheumatic or rheumatoid) diseases.

On the basis of their efficacy as inhibitors of VEGF-receptor tyrosine kinase activity the compounds of the formula I primarily inhibit the growth of blood vessels and are thus, for example, effective against a number of diseases associated with deregulated angiogenesis, especially diseases caused by ocular neovascularisation, especially retinopathies, such as diabetic retinopathy or age-related macular degeneration, psoriasis, haemangioblastoma, such as haemangioma, mesangial cell proliferative disorders, such as chronic or acute renal diseases, e.g. diabetic nephropathy, malignant nephrosclerosis, thrombotic microangio-pathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, endometriosis, chronic asthma, arterial or post-transplantational atherosclerosis, neurodegenerative disorders and especially neoplastic diseases like leukaemias, especially acute lymphoblastic leukaemia, acute myeloid leukaemia and chronic myeloid leukaemia, and other "liquid tumours", especially those expressing c-kit, KDR or flt-1, and solid tumours, especially breast cancer, cancer of the colon, lung cancer (especially small-cell lung cancer), cancer of the prostate or Kaposi's sarcoma. A compound of formula I (or an N-oxide thereof) inhibits the growth of tumours and is especially suited to preventing the metastatic spread of tumours and the growth of micrometastases.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. PKI166, the VEGF receptor tyrosine kinase, e.g. PTK787, or the PDGF receptor tyrosine kinase, e.g. STI571, a cytokine, a negative growth regulator, such as TGF-β or IFN-β, an aromatase inhibitor, e.g. letrozole or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel, discodermolide or an epothilone, alkylating agents, antineoplastic antimetabolites, such as gemcitabine or capecitabine, platin compounds, such as carboplatin or cisplatin, antiangiogenic compounds, gonadorelin agonists, anti-androgens, bisphosphonates, e.g. AREDIA® or ZOMETA®, and trastuzumab. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

With the groups of preferred compounds of formula I and N-oxides thereof mentioned hereinafter, definitions of substituents from the general definitions mentioned hereinbefore may reasonably be used, for example, to replace more general definitions with more specific definitions or especially with definitions characterized as being preferred.

Furthermore, the invention relates to the use of a compound of formula I, wherein the radicals and symbols have the meanings as defined above, or a N-oxide or a pharmaceutically acceptable salt thereof for the preparation of a pharmaceutical product for the treatment of retinopathy or age-related macula degeneration.

Furthermore, the invention relates to a method for the treatment of a neoplastic disease which responds to an inhibition of the VEGF-receptor tyrosine kinase activity, which comprises administering a compound of formula I or a N-oxide or a pharmaceutically acceptable salt thereof, wherein the radicals and symbols have the meanings as defined above, in a quantity effective against the said disease, to a warm-blooded animal requiring such treatment.

Furthermore, the invention relates to a method for the treatment of retinopathy or age-related macular degeneration, which comprises administering a compound of formula I or a N-oxide or a pharmaceutically acceptable salt thereof, wherein the radicals and symbols have the meanings as defined above, in a quantity effective against said diseases, to a warm-blooded animal requiring such treatment.

The invention relates in particular to a compound of formula I, wherein

Ar is represented by the subformula $I_a$ wherein $R_a$ represents H or lower alkyl, and $R_1$ represents H or trifluoromethyl, $R_2$ represents H, halogen, $C_2$–$C_7$alkyl, $C_2$–$C_7$alkenyl or lower alkynyl; or Ar is represented by the subformula $I_b$, and $R_1$ represents trifluoromethyl, and $R_2$ represents bromo, iodo, $C_2$–$C_7$alkyl, $C_2$–$C_7$alkenyl or lower alkynyl, or $R_1$ represents H, and $R_2$ represents fluoro, bromo, iodo, ethyl, $C_5$–$C_7$alkyl, $C_2$–$C_7$alkenyl or lower alkynyl, to an N-oxide or a tautomer thereof, or to a salt of such anthranilic acid amide, its N-oxide or its tautomer, Preferred are compounds of formula I, wherein Ar is represented by the subformula $I_a$ wherein $R_a$ represents H or lower alkyl, $R_1$ represents H or trifluoromethyl, and $R_2$ represents H, halogen, $C_2$–$C_7$alkyl, $C_2$–$C_7$alkenyl or lower alkynyl.

Also preferred are compounds of formula I, wherein

Ar is represented by the subformula $I_b$, $R_1$ represents trifluoromethyl, and $R_2$ represents bromo, iodo, $C_2$–$C_7$alkyl, $C_2$–$C_7$alkenyl or lower alkynyl, or $R_1$ represents H, and $R_2$ represents fluoro, bromo, iodo, ethyl, $C_5$–$C_7$alkyl, $C_2$–$C_7$alkenyl or lower alkynyl.

More preferred are compounds of formula I, wherein

Ar is represented by the subformula $I_b$, $R_1$ represents trifluoromethyl, and $R_2$ represents bromo, propyl, propenyl or propinyl, or $R_1$ represents H, and $R_2$ represents fluoro, bromo, propenyl or propinyl.

One embodiment of the invention pertains to anthranilic acid amide of formula I, wherein Ar is represented by the N-oxide of subformula $I_b$, $R_1$ represents trifluoromethyl, $R_2$ represents bromo, propyl, propenyl or propinyl.

More specifically, preference is given to the following compounds of formula I:

2-[4-Pyridinylmethyl]amino-N-[4-bromo-3-(trifluoromethyl)phenyl]benzamide,
2-[4-Pyridinylmethyl]amino-N-(4-bromophenyl)benzamide,
2-[[3-[(methylamino)carbonyl]-phenyl]methyl]amino-N-[3-(trifluoromethyl)phenyl]benzamide,
2-[4-Pyridinylmethyl]amino-N-[4-(1-propynyl)-3-(trifluoromethyl)phenyl]benzamide,
2-[4-Pyridinylmethyl]amino-N-[4-(1-propynyl)phenyl]benzamide,
2-[4-Pyridinylmethyl]amino-N-[4-[(Z)-1-propenyl]-3-(trifluoromethyl)phenyl]benzamide hydrochloride salt,
2-[4-Pyridinylmethyl]amino-N-[4-(1-propyl)-3-(trifluoromethyl)phenyl]benzamide,
N-(4-Chloro-3-trifluoromethyl-phenyl)-2-[(1-oxy-pyridin-4-ylmethyl)-amino]-benzamide, and
N-(4-Fluoro-3-trifluoromethyl-phenyl)-2-[(1-oxy-pyridin-4-ylmethyl)-amino]-benzamide, and the tautomers thereof, or a salt of such compound or its tautomer.

A compound of the invention may be prepared by processes that, though not applied hitherto for the new compounds of the present invention, are known per se, especially a process characterized in that for the synthesis of a compound of the formula I wherein $R_2$ represents hydrogen or halogen and the remaining symbols $R_1$ and Ar are as defined above for a compound of the formula I, a compound of the formula II

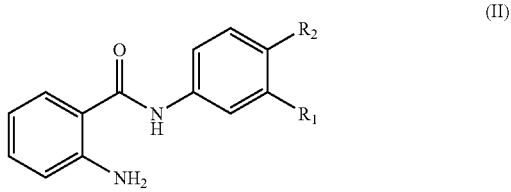

wherein $R_1$ and $R_2$ are as defined above, is reacted with a carbonyl compound of the formula III

wherein Ar is as defined above for a compound of formula I in the presence of a reducing agent, wherein the starting compounds of formula II and III may also be present with functional groups in protected form, if necessary, and/or in the form of salts, provided a salt-forming group is present and the reaction in salt form is possible;

wherein any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

Alternatively, a compound of formula II can be reacted with a compound of formula III in the presence of an acid, e.g. camphor-10-sulfonic acid, in a suitable solvent like toluene or benzene at reflux temperature between about 15 minutes and 6 hours providing a bicyclic compound of formula IV,

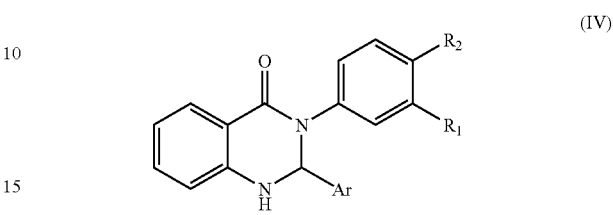

wherein $R_2$ represents hydrogen or halogen and the remaining symbols $R_1$ and Ar are as defined above for a compound of the formula I, which bicyclic compound of formula IV can be further reacted in a suitable solvent with triethylsilane and trifluoroacetic acid at a temperature between 60° C. and 90° C. for a duration between 4 and 12 hours providing a compound of formula I wherein $R_2$ represents hydrogen or halogen and the remaining symbols $R_1$ and Ar are as defined above for a compound of the formula I.

Detailed Description of the Reductive Alkylation:

In the more detailed description of the process below, $R_1$, $R_2$ and Ar are as defined for compounds of formula I, unless otherwise indicated.

The carbonyl compound of the formula III may also be present in the form of reactive derivative; however, the free aldehyde or ketone is preferred.

Reactive derivatives of the compounds of formula III are, for example, corresponding bisulfite adducts or especially semiacetals, acetals, semiketals or ketals of compounds of formula III with alcohols, for example lower alkanols; or thioacetals or thioketals of compounds of formula III with mercaptans, for example lower alkanesulfides.

The reductive alkylation is preferably carried out with hydrogenation in the presence of a catalyst, especially a noble metal catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkanecarboxylic acids, especially acetic acid, or a sulfonic acid, such as p-toluenesulfonic acid; in customary solvents, for example alcohols, such as methanol or ethanol, or ethers, for example cyclic ethers, such as tetrahydrofuran, in the presence or absence of water.

Protecting Groups

If one or more other functional groups, for example carboxy, hydroxy, amino, or mercapto, are or need to be protected in a compound of formulae II or II, because they should not take part in the reaction, these are such groups as are usually used in the sythesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Additional Process Steps

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

An anthranilic acid amide of formula I wherein $R_2$ represents halogen, preferably bromide, can be further reacted in accordance with the following process.

An anthranilic acid amide of formula I wherein $R_2$ represents halogen is solved in a suitable aromatic solvent like benzene, toluene or xylene and reacted with a stannane of formula VIII,

(VII)

wherein $R_3$ is H or lower alkyl, in the presence of a suitable catalyst, preferably tetrakis(triphenylphosphine)palladium (0), at a temperature between 90° C. and 150° C., preferably under an argon atmosphere, between 12 and 36 hours in a suitable aromatic solvent like benzene, toluene or xylene.

The obtained compound of formula I wherein $R_2$ represents the alkynyl radical —C≡C—$R_3$ can be transformed into a corresponding alkenyl or alkyl radicals by reactions known in the art.

For example, a compound of formula I wherein $R_2$ represents the alkynyl radical —C≡C—$R_3$ can be hydrogenated in methanol at atmospheric pressure over Raney nickel at a temperatur between 15° C. and 30° C., to provide a compound of formula I wherein $R_2$ represents $C_{2-7}$alkenyl. Such resulting compound of formula I wherein $R_2$ represents $C_{2-7}$alkenyl can be further hydrogenated in methanol at atmospheric pressure over 5% platinum on carbon at a temperatur between 15° C. and 30° C., to provide a compound of formula I wherein $R_2$ represents $C_{2-7}$alkyl.

| Abbreviations: | |
|---|---|
| DMF | dimethylformamide |
| EtOAc | ethyl acetate |
| MS | mass spectra |
| RT | room temperature |
| TLC | thin layer chromatogram |

The following Examples serve to illustrate the invention without limiting the invention in its scope. Temperatures are measured in degrees celsius (° C.). Unless otherwise indicated, the reactions take place at room temperature.

EXAMPLES

Reference Example 1

2-[[6-Methoxy-3-pyridinyl]methyl]amino-N-[4-bromo-3-(trifluoromethyl)phenyl]benzamide (not claimed)

Sodium cyanoborohydride (8.80 g of 95%, 133 mmol) is added in portions over 30 minutes to a stirred mixture of acetic acid (3.8 mL), 6-methoxy-3-pyridinecarboxaldehyde (Fluka, Buchs, Switzerland; 7.80 g, 57 mmol) and 2-amino-N-(4-bromo-3-trifluoromethylphenyl)benzamide (step 1.2; 13.65 g, 38 mmol) in methanol (380 mL) at 25° C. The mixture is stirred for 16 hours. The solvent is evaporated under reduced pressure to give a residue which is treated with a saturated aqueous solution of sodium hydrogen carbonate (500 mL) and extracted with dichloromethane (3×150 mL). The combined extracts are dried ($Na_2SO_4$), filtered and the solvent is evaporated under reduced pressure to yield the crude product that is purified by column chromatography on silica gel, eluent 5% EtOAc in dichloromethane and recrystallised from diethylether-hexane to give the title compound as a beige crystalline solid, m.p. 101–103° C.

Step 1.1: 2-Nitro-N-(4-bromo-3-trifluoromethylphenyl)benzamide

A solution of 3-amino-6-bromobenzotrifluoride (Fluka, Buchs, Switzerland; 24.0 g, 100 mmol) in EtOAc (240 mL) is added to a stirred aqueous solution of sodium hydroxide (110 mL of 1 M) at room temperature. This stirred solution is then treated dropwise over 30 minutes with a solution of 2-nitrobenzoyl chloride (Fluka, Buchs, Switzerland; 14.5 mL, 110 mmol) in EtOAc (150 mL). The resulting mixture is then stirred for 30 min at ambient temperature. The mixture is extracted with EtOAc (3×100 mL) and the combined extracts are sequentially washed with hydrochloric acid (2×100 mL of 2M), water (2×100 mL), saturated aqueous sodium hydrogen carbonate solution (2×100 mL) and saturated aqueous sodium chloride (1×100 mL), dried (MgSO$_4$), filtered and the solvent is evaporated under reduced pressure to yield the crude product which is purified by recrystallisation from EtOAc-hexane to give the title compound as a beige crystalline solid, m.p. 157–158° C.

Step 1.2: 2-Amino-N-(4-bromo-3-trifluoromethylphenyl)benzamide

A solution of 2-nitro-N-(4-bromo-3-trifluoromethylphenyl)benzamide (intermediate 1a; 32 g, 82 mmol) in methanol (1000 mL) is hydrogenated at atmospheric pressure over Raney nickel (6 g) at 21° C. The calculated amount of hydrogen is taken up after 7 hours. The mixture is filtered and the solvent is evaporated under reduced pressure to yield the crude product which is purified by recrystallisation from diethylether-hexane to give the title compound as a colourless crystalline solid, m.p. 142–144° C.

Example 2

2-[4-Pyridinylmethyl]amino-N-[4-bromo-3-(trifluoromethyl)phenyl]benzamide

The title compound is prepared by a method analogous to that described in Example 1 by utilising the intermediate from step 1.2 and 4-pyridinecarboxaldehyde; m.p. 123–124° C.

Example 3

2-[4-Pyridinylmethyl]amino-N-(4-bromophenyl)benzamide

The title compound is prepared by a method analogous to that described in Example 1 by utilising the intermediate from step 3.2 and 4-pyridinecarboxaldehyde; m.p. 136–137° C.

Step 3.1: 2-Nitro-N-(4-bromophenyl)benzamide

The title compound is prepared analogously to step 1.1 by utilising 4-bromoaniline (Fluka, Buchs, Switzerland); m.p. 202–205° C.

Step 3.2: 2-Amino-N-(4-bromophenyl)benzamide

The title compound is prepared analogously to step 1.2 by utilising 2-nitro-N-(4-bromophenyl)benzamide (step 3.1); m.p. 139–144° C.

Example 4

2-[[3-[(methylamino)carbonyl]-phenyl]methyl]amino-N-[3-(trifluoromethyl)phenyl]-benzamide The title compound is prepared by a method analogous to that described in Example 1 by utilising the intermediate from step 4.2 and 3-formyl-N-methyl-benzamide (prepared according to the method described in WO 98/14449); m.p. 166–167° C.

Step 4.1: 2-Nitro-N-[3-(trifluoromethyl)phenyl]benzamide

The title compound is prepared analogously to step 1.1 by utilising 3-(trifluoromethyl)-benzenamine (Aldrich, Buchs, Switzerland); m.p. 134–135° C.

Step 4.2: 2-Amino-N-[(3-trifluoromethyl)phenyl)benzamide

The title compound is prepared analogously to step 1.2 by utilising 2-nitro-N-[(3-trifluoromethyl)phenyl)benzamide (step 2.1); m.p. 132–133° C.

Reference Example 5

2-[[6-Methoxy-3-pyridinyl]methylamino-N-[4-(1-propynyl)-3-(trifluoromethyl)phenyl]benzamide (not claimed)

A stirred solution of 2-[[6-methoxy-3-pyridinyl]methyl]amino-N-[4-bromo-3-(trifluoromethyl)-phenyl]-benzamide (Example 1; 3.98 g, 8.3 mmol) in dry toluene (200 mL) is purged with argon for 20 minutes at 25° C. Tributyl-1-propynylstannane (4.1 g of 80%, 9.96 mmol) and tetrakis(triphenylphosphine)palladium (0) (260 mg) are then added and the resulting mixture is heated at 100° C. for 17 hours under an argon atmosphere. The mixture is then cooled, treated with an aqueous solution of sodium hydroxide (85 mL of 0.1 M) and purged with air for 2 hours. The resulting mixture is extracted with EtOAc (3×100 mL). The organic phase is sequentially washed with water (2×40 mL) and saturated aqueous sodium chloride (1×40 mL), dried (Na$_2$SO$_4$), filtered and the solvent is evaporated under reduced pressure to yield the crude product which is purified by column chromatography on silica gel, eluent 33% EtOAc in hexane and recrystallised from diethylether-hexane to give the title compound as a pale-yellow crystalline solid; m.p. 123–124° C.

Example 6

2-[4-Pyridinylmethyl]amino-N-[4-(1-propynyl)-3-(trifluoromethyl)phenyl]-benzamide The title compound is prepared by a method analogous to that described in Example 5 by utilising 2-[4-pyridinylmethyl]amino-N-[4-bromo-3-(trifluoromethyl)phenyl]benzamide (Example 2); m.p. 165–166° C.

Example 7

2-[4-Pyridinylmethyl]amino-N-[4-(1-propynyl)phenyl]benzamide

The title compound is prepared by a method analogous to that described in Example 5 by utilising 2-[4-pyridinylmethyl]amino-N-[4-bromophenyl]benzamide (Example 3); m.p. 147–155° C.

Example 8

2-[4-Pyridinylmethyl]amino-N-[4-[(Z)-1-propenyl]-3-(trifluoromethyl)-phenyl]benzamide hydrochloride salt A solution of 2-[4-pyridinylmethyl]amino-N-[4-(1-propynyl)-3-(trifluoromethyl)phenyl]benzamide (Example 6; 0.13 g, 0.32 mmol) in methanol (6 mL) is hydrogenated at atmospheric pressure over Raney nickel (50 mg) at 22° C.

Hydrogen uptake is taken up after 7 hours. The mixture is then filtered and the solvent is evaporated under reduced pressure to yield the crude product which is purified by column chromatography on silica gel, eluent 50% EtOAc in dichloromethane to give the product as an oil. The oil dissolved in ethanol, acidified with a solution of hydrogen chloride in EtOAc (2 M) and diluted with diethylether. The resulting precipitate is filtered off, washed with diethylether, dried and purified by recrystallisation from diethylether-ethanol to give the title compound as a beige solid.

Example 9

2-[4-Pyridinylmethyl]amino-N-[4-(1-propyl)-3-(trifluoromethyl)phenyl]benzamide

A solution of 2-[4-pyridinylmethyl]amino-N-[4-[(Z)-1-propenyl]-3-(trifluoromethyl)phenyl]benzamide (Example 8; 0.80 g, 1.75 mmol) in methanol (25 mL) is hydrogenated at atmospheric pressure over 5% platinum on carbon (0.2 g) at 22° C. The calculated amount of hydrogen is taken up after 12 hours. The mixture is then filtered and the solvent is evaporated under reduced pressure to yield the crude product which is purified by column chromatography on silica gel, eluent 20% dichloromethane in EtOAc and recrystallised from diethylether-hexane to give the title compound as a colourless crystalline solid; m.p. 134–135° C.

Example 10

N-(4-Chloro-3-trifluoromethyl-phenyl)-2-[(1-oxy-pyridin-4-ylmethyl)-amino]-benzamide Under $N_2$-atmosphere, 0.50 g (1.2 mMol) of rac. 3-(4-chloro-3-trifluoromethyl-phenyl)-2-(1-oxy-pyridin-4-yl)-2,3-dihydro-1H-quinazolin-4-one are suspended in 8 ml of ice-cooled 1,2-dichloroethane. 0.47 ml (3.0 mMol) of triethylsilane are added, followed after 5 min by 0.56 ml (7.2 mMol) of trifluoroacetic acid. The resulting solution is stirred for 7 h at 80° C., cooled to RT and diluted with 100 ml of EtOAc. Then the solution is washed twice with saturated $NaHCO_3$ solution and brine. The aqueous layers are extracted 2 times with EtOAc, the organic phases dried ($Na_2SO_4$) and concentrated partially in vacuuo until the product crystallizes. Filtration and washing with EtOAc gives the title compound; m.p. 213–214° C. Additional product can be obtained from the filtrate by column chromatography ($SiO_2$; EtOAc/MeOH 8:2).

Step 10.1: rac. 3-(4-Chloro-3-trifluoromethyl-phenyl)-2-(1-oxy-pyridin-4-yl)-2,3-dihydro-1H-quinazolin-4-one A suspension of 10.04 g (31.9 mMol) of 2-amino-N-[4-chloro-3-trifluoromethyl)phenyl]benzamide (preparation see WO 00/27820; intermediate 2f) in 80 ml of toluene is prepared in a vessel with water separation equipment. 3.93 g (31.9 mMol) of 1-oxy-pyridine-4-carbaldehyde and 23 mg of camphor-10-sulfonic acid are added. The mixture is heated up to 120° C. for 1 h. After cooling to RT, the reaction mixture is filtered and the obtained residue washed with toluene and diethyl ether, yielding the title compound; m.p. 261–262° C.

Example 11

N-(4-Fluoro-3-trifluoromethyl-phenyl)-2-[(1-oxy-pyridin-4-ylmethyl)-amino]-benzamide Under $N_2$-atmosphere, 1.50 g (3.7 mMol) of rac. 3-(4-fluoro-3-trifluoromethyl-phenyl)-2-(1-oxy-pyridin-4-yl)-2,3-dihydro-1H-quinazolin-4-one are suspended in 25 ml of ice-cold dichloromethane. Then 0.83 ml (5.2 mMol) of triethylsilane are added, followed by 1.79 ml (23 mMol) of trifluoroacetic acid. The resulting solution is stirred for 72 h at RT, then additional 0.42 ml of triethylsilane are added. After totally 138 h at RT, the solution is diluted with 300 ml of EtOAc and 300 ml of saturated $NaHCO_3$ solution. The aqueous layer is separated off and extracted twice with EtOAc. The organic phases are washed with saturated $NaHCO_3$ solution and brine, dried ($Na_2SO_4$) and concentrated. The residue is dissolved in methanol, $SiO_2$ is added and the mixture concentrated. The resulting powder is put on a chromatography column ($SiO_2$). Eluation with acetone/EtOH 3:1 gives the title compound; m.p. 182–184° C.

Step 11.1: rac. 3-(4-Fluoro-3-trifluoromethyl-phenyl)-2-(1-oxy-pyridin-4-yl)-2,3-dihydro-1H-quinazolin-4-one Condensation of 2.42 g (8.1 mMol) of 2-amino-N-[4-fluoro-3-trifluoromethyl)phenyl]-benzamide (preparation see WO 00/27820; intermediate 2h) and 980 mg (7.96 mMol) of 1-oxy-pyridine-4-carbaldehyde in 20 ml of toluene and 5 mg of camphor-10-sulfonic analogously to Step 10.1 gives the title compound; m.p. 257–258° C.

Example 12

Soft Capsules 5000 soft gelatin capsules, each comprising as active ingredient 0.05 g of one of the compounds of formula I mentioned in the preceding Examples, are prepared as follows:

| Composition | |
|---|---|
| Active ingredient | 250 g |
| Lauroglycol | 2 litres |

Preparation process: The pulverized active ingredient is suspended in Lauroglykol® (propylene glycol laurate, Gattefossé S.A., Saint Priest, France) and ground in a wet pulverizer to produce a particle size of about 1 to 3 µm. 0.419 g portions of the mixture are then introduced into soft gelatin capsules using a capsule-filling machine.

The invention claimed is:
1. An anthranilic acid amide of formula I,

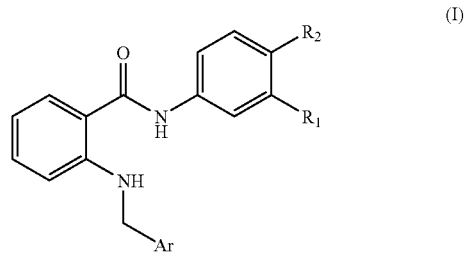

wherein Ar is represented by the subformula $I_a$

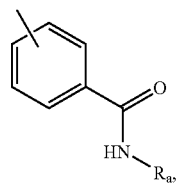

(Iₐ)

wherein R_a represents H or lower alkyl, and
R₁ represents H or perfluoro lower alkyl, and
R₂ represents H, halogen, C₂–C₇alkyl, C₂–C₇alkenyl or lower alkynyl; or
Ar is represented by the subformula I_b, and

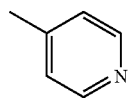

(I_b)

R₁ represents perfluoro lower alkyl, and
R₂ represents bromo, iodo, C₂–C₇alkyl, C₂–C₇alkenyl or lower alkynyl, or
R₁ represents H, and
R₂ represents fluoro, bromo, iodo, ethyl, C₅–C₇alkyl, C₂–C₇alkenyl or lower alkynyl,
or an N-oxide or a tautomer thereof,
or a salt of such anthranilic acid amide, its N-oxide or its tautomer.

2. An anthranilic acid amide of formula I according to claim 1, wherein
Ar is represented by the subformula I_a
wherein R_a represents H or lower alkyl, and
R₁ represents H or trifluoromethyl, and
R₂ represents H, halogen, C₂–C₇alkyl, C₂–C₇alkenyl or lower alkynyl; or
Ar is represented by the subformula I_b, and
R₁ represents trifluoromethyl, and
R₂ represents bromo, iodo, C₂–C₇alkyl, C₂–C₇alkenyl or lower alkynyl, or
R₁ represents H, and
R₂ represents fluoro, bromo, iodo, ethyl, C₅–C₇alkyl, C₂–C₇alkenyl or lower alkynyl,
or an N-oxide or a tautomer thereof,
or a salt of such anthranilic acid amide, its N-oxide or its tautomer.

3. An anthranilic acid amide of formula I according to claim 1, wherein
Ar is represented by the subformula I_a
wherein R_a represents H or lower alkyl,
R₁ represents H or trifluoromethyl, and
R₂ represents H, halogen, C₂–C₇alkyl, C₂–C₇alkenyl or lower alkynyl,
or a tautomer thereof,
or a salt of such anthranilic acid amide or its tautomer.

4. An anthranilic acid amide of formula I according to claim 1, wherein
Ar is represented by the subformula I_b,
R₁ represents trifluoromethyl, and
R₂ represents bromo, iodo, C₂–C₇alkyl, C₂–C₇alkenyl or lower alkynyl, or
R₁ represents H, and
R₂ represents fluoro, bromo, iodo, ethyl, C₅–C₇alkyl, C₂–C₇alkenyl or lower alkynyl,
or an N-oxide or a tautomer thereof,
or a salt of such anthranilic acid amide or N-oxide or its tautomer.

5. An anthranilic acid amide of formula I according to claim 4, wherein
Ar is represented by the subformula I_b,
R₁ represents trifluoromethyl, and
R₂ represents bromo, propyl, propenyl or propinyl, or
R₁ represents H, and
R₂ represents fluoro, bromo, propenyl or propinyl,
or an N-oxide or a tautomer thereof,
or a salt of such anthranilic acid amide or N-oxide or its tautomer.

6. An anthranilic acid amide of formula I according to claim 4, wherein
Ar is represented by the N-oxide of subformula I_b,
R₁ represents trifluoromethyl, and
R₂ represents bromo, propyl, propenyl or propinyl,
or a tautomer thereof,
or a salt of such anthranilic acid amide or its tautomer.

7. An anthranilic acid amide of formula I according to claim 1 selected from
2-[4-Pyridinylmethyl]amino-N-[4-bromo-3-(trifluoromethyl)phenyl]benzamide,
2-[4-Pyridinylmethyl]amino-N-(4-bromophenyl)benzamide,
2-[[3-[(methylamino)carbonyl]-phenyl]methyl]amino-N-[3-(trifluoromethyl)phenyl]benzamide,
2-[4-Pyridinylmethyl]amino-N-[4-(1-propynyl)-3-(trifluoromethyl)phenyl]benzamide,
2-[4-Pyridinylmethyl]amino-N-[4-(1-propynyl)phenyl]benzamide,
2-[4-Pyridinylmethyl]amino-N-[4-[(Z)-1-propenyl]-3-(trifluoromethyl)phenyl]benzamide hydrochloride salt,
2-[4-Pyridinylmethyl]amino-N-[4-(1-propyl)-3-(trifluoromethyl)phenyl]benzamide,
N-(4-Chloro-3-trifluoromethyl-phenyl)-2-[(1-oxy-pyridin-4-ylmethyl)-amino]-benzamide, and
N-(4-Fluoro-3-trifluoromethyl-phenyl)-2-[(1-oxy-pyridin-4-ylmethyl)-amino]-benzamide,
or an N-oxide or a tautomer thereof,
or a salt of such anthranilic acid amide, its N-oxide or its tautomer.

8. An anthranilic acid amide of formula I according to claim 1, or an N-oxide or a tautomer thereof, or a pharmaceutically acceptable salt of such a compound, for use in a method for the treatment of the human or animal body.

9. A pharmaceutical composition comprising an anthranilic acid amide of formula I according to claim 1, or an N-oxide or a tautomer thereof, or a pharmaceutically acceptable salt of such a compound, or a hydrate or solvate thereof, and at least one pharmaceutically acceptable carrier.

10. A process for the preparation of an anthranilic acid amide of formula I

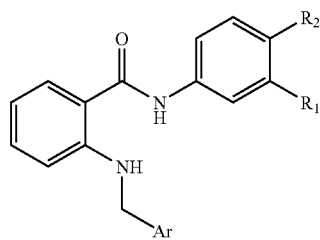

wherein $R_2$ represents hydrogen or halogen and the remaining symbols $R_1$ and Ar are as defined in claim 1, wherein a compound of the formula II

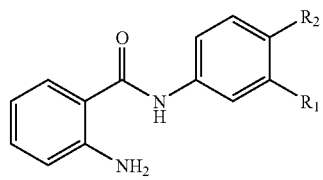

wherein $R_1$ and $R_2$ are as defined above for formula I, is reacted with a carbonyl compound of the formula III

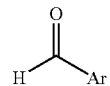

wherein Ar is as defined above for a compound of formula I in the presence of a reducing agent, wherein the starting compounds of formula II and III may also be present with functional groups in protected form, if necessary, and/or in the form of salts, provided a salt-forming group is present and the reaction in salt form is possible;

wherein any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

\* \* \* \* \*

UNITED STATES PATENT AND TRADEMARK OFFICE
CERTIFICATE OF CORRECTION

PATENT NO. : 7,067,543 B2  
APPLICATION NO. : 10/494222  
DATED : June 27, 2006  
INVENTOR(S) : Bold et al.

Page 1 of 1

It is certified that error appears in the above-identified patent and that said Letters Patent is hereby corrected as shown below:

On the title page

Item (30) should read:

-- Foreign Application Priority Data
Nov. 8, 2001  (GB).............................0126901.8
June 5, 2002  (GB).............................0212917.9 --.

Signed and Sealed this

Nineteenth Day of December, 2006

JON W. DUDAS
*Director of the United States Patent and Trademark Office*